United States Patent
Fu

(10) Patent No.: US 10,610,202 B2
(45) Date of Patent: Apr. 7, 2020

(54) ULTRASONIC IMAGING SYSTEM AND CONTROLLING METHOD THEREOF

(71) Applicant: SHENZHEN MINDRAY BIO-MEDICAL ELECTRONICS CO., LTD., Shenzhen (CN)

(72) Inventor: Zhengpeng Fu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 504 days.

(21) Appl. No.: 15/269,673

(22) Filed: Sep. 19, 2016

(65) Prior Publication Data

US 2017/0007212 A1  Jan. 12, 2017

Related U.S. Application Data

(63) Continuation of application No. PCT/CN2014/084256, filed on Aug. 13, 2014.

(51) Int. Cl.
| | |
|---|---|
| *A61B 8/00* | (2006.01) |
| *G06F 3/01* | (2006.01) |
| *G06F 3/0484* | (2013.01) |
| *G06F 3/0488* | (2013.01) |

(52) U.S. Cl.
CPC ............. *A61B 8/54* (2013.01); *A61B 8/465* (2013.01); *A61B 8/467* (2013.01); *A61B 8/58* (2013.01); *G06F 3/017* (2013.01); *G06F 3/04847* (2013.01); *G06F 3/04883* (2013.01)

(58) Field of Classification Search
CPC .. A61B 8/54; A61B 8/58; A61B 8/467; A61B 8/465; G06F 3/017; G06F 3/04883; G06F 3/04847

USPC .................................................. 600/437–469
See application file for complete search history.

(56) References Cited

U.S. PATENT DOCUMENTS

| | | | |
|---|---|---|---|
| 9,423,886 B1* | 8/2016 | Neglur | G06F 3/017 |
| 10,281,987 B1* | 5/2019 | Yang | G06F 3/04847 |
| 2002/0128554 A1 | 9/2002 | Seward | |
| 2008/0114615 A1* | 5/2008 | Mahesh | G06Q 10/10 705/2 |
| 2011/0260965 A1* | 10/2011 | Kim | G06F 3/013 345/156 |

(Continued)

FOREIGN PATENT DOCUMENTS

| | | |
|---|---|---|
| CN | 101119680 A | 2/2008 |
| CN | 202776368 U | 3/2013 |

(Continued)

*Primary Examiner* — Sanjay Cattungal
(74) *Attorney, Agent, or Firm* — Kory D. Christensen

(57) ABSTRACT

The present disclosure discloses a system and method for ultrasonic imaging. The method includes receiving a user-defined control gesture and associating the control gesture with a function selected by a user; forming a control gesture signal and function association database; when the ultrasonic imaging system is in normal operation, receiving a current control gesture signal and matching the current control gesture with a control gesture in the database to determine a function associated with the matched control gesture; and controlling the ultrasonic imaging system to perform the associated function. According to the present disclosure, it is very convenient for users to define customized control gestures according to their personal operation routines and habits.

12 Claims, 2 Drawing Sheets

(56) References Cited

U.S. PATENT DOCUMENTS

| | | | | |
|---|---|---|---|---|
| 2012/0235940 | A1* | 9/2012 | Ludwig | G10H 1/00 |
| | | | | 345/173 |
| 2014/0071069 | A1* | 3/2014 | Anderson | A63F 13/06 |
| | | | | 345/173 |
| 2014/0088428 | A1* | 3/2014 | Yang | A61B 8/4444 |
| | | | | 600/443 |
| 2014/0121524 | A1* | 5/2014 | Chiang | G16H 30/20 |
| | | | | 600/459 |
| 2014/0121525 | A1 | 5/2014 | Kusaka | |
| 2014/0128739 | A1* | 5/2014 | Sundaran | A61B 8/4254 |
| | | | | 600/459 |
| 2014/0194742 | A1* | 7/2014 | Sundaran Baby Sarojam | |
| | | | | A61B 8/54 |
| | | | | 600/459 |
| 2014/0201666 | A1* | 7/2014 | Bedikian | G06F 3/017 |
| | | | | 715/771 |
| 2014/0221836 | A1* | 8/2014 | Takeda | A61B 8/463 |
| | | | | 600/443 |
| 2014/0282274 | A1* | 9/2014 | Everitt | G06F 3/017 |
| | | | | 715/863 |
| 2014/0282282 | A1* | 9/2014 | Holz | G06F 3/017 |
| | | | | 715/863 |
| 2015/0220150 | A1* | 8/2015 | Plagemann | G06F 3/017 |
| | | | | 715/856 |
| 2015/0327841 | A1* | 11/2015 | Banjanin | A61B 8/5276 |
| | | | | 600/443 |

FOREIGN PATENT DOCUMENTS

| | | |
|---|---|---|
| CN | 202932946 U | 5/2013 |
| CN | 103767721 A | 5/2014 |

* cited by examiner

ULTRASONIC IMAGING SYSTEM AND CONTROLLING METHOD THEREOF

TECHNICAL FIELD

The present disclosure relates to the medical ultrasonic imaging field, particularly to an ultrasonic imaging system and a controlling method thereof.

BACKGROUND

With the development of ultrasonic technology, ultrasonic diagnostic equipment has been accepted by clinicians in various application fields, and has gradually become daily-use diagnostic equipment. As the popularity of ultrasonic diagnostic equipment in various clinical departments grows, the clinicians' requirements for convenience and specialty operation of the equipment are increasing.

But the design of the existing control panel and user interface (UI) is limited. Only some frequently-used function buttons are placed in prominent areas or first-level menus, where clinicians can operate them conveniently. Clinicians in various clinical departments focus on different functions and have different operation routines. Therefore, a unified panel and UI design can hardly satisfy the demand of clinicians in various clinical departments.

In order to solve the above-mentioned problem, most manufacturers deploy one or two reserved user-defined buttons in their control panel designs. Clinicians can define the functions of the user-defined buttons according to their own operation routine. Nevertheless, one or two reserved user-defined buttons are insufficient to solve the problem.

Besides, in some other, related arts, all the buttons on the control panel are user-defined buttons, functions of which can be completely defined by users. This kind of design may satisfy the demand of clinicians in various clinical departments. But the operation may be relatively complex. Furthermore, after the redefinition of the buttons, it would take a long time for the clinicians to remember the new locations of these buttons.

SUMMARY

One of the objects of the present disclosure is to provide an ultrasonic imaging system and a controlling method to enable clinicians to conveniently control the ultrasonic imaging system and operate the system according to their customized operation routines.

In some embodiments, a method for controlling an ultrasonic imaging system is provided. The method may include: receiving an associated function selection signal, where at least one function of the ultrasonic imaging system is selected by the associated function selection signal; acquiring a control gesture signal; associating the control gesture signal with the at least one function selected by the associated function selection signal to obtain an association correlation between the control gesture signal and the at least one function; storing the control gesture signal and the association correlation and forming a control gesture signal and function association database; and when the ultrasonic imaging system is in normal operation, receiving a current control gesture signal, searching in the control gesture signal and function association database for a control gesture signal matching the current control gesture signal to obtain a matched control gesture signal, determining at least one function associated with the matched control gesture signal according to the association correlation of the matched control gesture signal, and controlling the ultrasonic imaging system to execute the at least one function associated with the matched control gesture signal.

In one embodiment of the present disclosure, acquiring the control gesture signal may include selecting the control gesture signal from a pre-stored control gesture signal database.

In one embodiment of the present disclosure, acquiring a control gesture signal may include receiving the control gesture signal input by a user.

In one embodiment of the present disclosure, the control gesture signal may be a signal generated by a slide operation of the user on a touch screen.

In one embodiment of the present disclosure, the control gesture signal may be a signal generated by a body motion sensor which detects body movement of the user.

In one embodiment of the present disclosure, the control gesture signal and function association database may contain at least one control gesture signal and an association correlation between the control gesture signal and a function of the ultrasonic imaging system.

In some embodiments of the present disclosure, an ultrasonic imaging system is provided. The ultrasonic imaging system may include a control unit, a first input unit and a second input unit.

The first input unit may be connected with the control unit, where the first input unit may be used to detect an input current control gesture and to output a current control gesture signal when the ultrasonic imaging system is in normal operation. The second input unit may be connected with the control unit, where the second input unit may be used to input an associated function selection signal, and the associated function selection signal may be used to select at least one function of the ultrasonic imaging system.

The control unit may be used to receive the associated function selection signal from the second input unit, receive the control gesture signal, associate the control gesture signal and the at least one function selected by the associated function selection signal to obtain the association correlation between the control gesture signal and the at least one function of the ultrasonic imaging system, and store the control gesture signal and the association correlation to form a control gesture signal and function association database. When the ultrasonic imaging system is in normal operation, the control unit may further be used to receive the current control gesture signal from the first input unit, search for the control gesture signal matching the current control gesture signal in the control gesture signal and function association database to obtain a matched control gesture signal, determine at least one function associated with the matched control gesture signal according to the association correlation of the matched control gesture signal, and control the ultrasonic imaging system to perform the at least one function associated with the matched control gesture signal.

In one embodiment of the present disclosure, the control unit may be used to select the control gesture signal from a pre-stored control gesture signal database.

In one embodiment of the present disclosure, the control unit may be used to acquire the control gesture signal based on a control gesture input by a user through the first input unit.

In one embodiment of the present disclosure, the first input unit may be a touch screen.

In one embodiment of the present disclosure, the first input unit may be a body motion controller.

In one embodiment of the present disclosure, the control gesture signal and function association database may include at least one control gesture signal and an association correlation between the control gesture signal and a function of the ultrasonic imaging system.

According to embodiments of the present disclosure, clinicians are enabled to define personalized control gestures according to their own operation routines and habits to form an association correlation database of control gesture signals and functions, such that when the ultrasonic imaging system is in operation, clinicians may control the ultrasonic imaging system by simply performing the control gestures to control the ultrasonic imaging system such that it executes the corresponding functions. Therefore, it is unnecessary for clinicians to pay attention to the keyboard on the control panel; clinicians can instead focus on the images on the monitor or the control of the probe. Therefore, the present disclosure greatly facilitates user operation.

DETAILED DESCRIPTION

Figure 1:
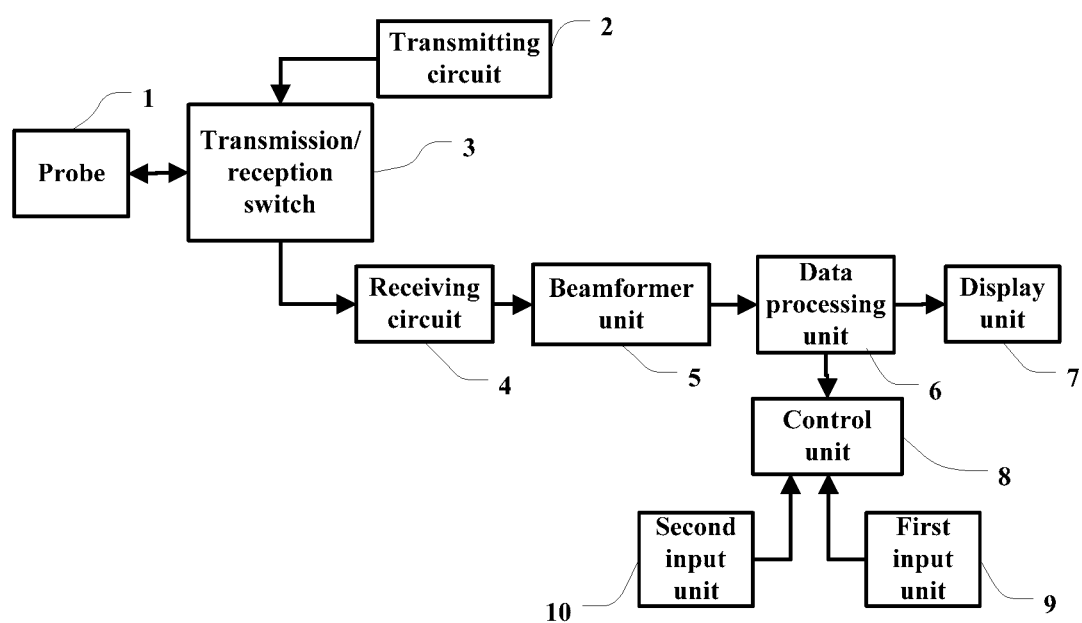
FIG. 1 is a schematic diagram of an ultrasonic imaging system according to one embodiment of the present disclosure.

FIG. 1 is a schematic diagram of an ultrasonic imaging system according to one embodiment of the present disclosure. Referring to FIG. 1, the ultrasonic imaging system may include a probe 1, a transmitting circuit 2, a transmission/reception switch 3, a receiving circuit 4, a beamformer unit 5, a data processing unit 6 and a display unit 7.

During the ultrasonic imaging process, the transmitting circuit 2 transmits emitting pulses, which have been delay focused and have certain magnitude and polarity, to the probe 1 through the transmission/reception switch 3. Excited by the emitting pulses, the probe 1 emits ultrasound waves to a scan target (e.g., a human or animal body, organs, tissues, blood vessels, etc., not shown in the figures), and receives ultrasonic echoes containing information of the scan target after a certain delay, then transforms the ultrasonic echoes into electric signals. The receiving circuit 4 receives the electric signals transformed by the probe 1 to obtain ultrasonic echo signals, and transmits the ultrasonic echo signals into the beamformer unit 5. The beamformer unit 5 performs focusing delay, weighted summing and channel summing, and other processing of the ultrasonic echo signals, and then transmits the ultrasonic echo signals to the data processing unit 6. The data processing unit 6, according to different user-desired imaging modes, processes the signals with different algorithms, and different modes of image data are obtained. After certain processing such as logarithmic compression, dynamic range adjustment, and/or digital scan conversion, ultrasound images of different modes are generated, such as B-mode images, C-mode images, D-mode images and the like. The generated ultrasound images are transmitted to the display unit 7 for displaying.

In one embodiment of the present disclosure, the ultrasonic imaging system may further include a control unit 8, a first input unit 9, and a second input unit 10. The first input unit 9 and the second input unit 10 are connected to the control unit 8. The control unit 8, the first input unit 9 and the second input unit 10 may be used to implement the embodiment of the method of controlling an ultrasonic imaging system, which will be described in detail below.

Figure 2:
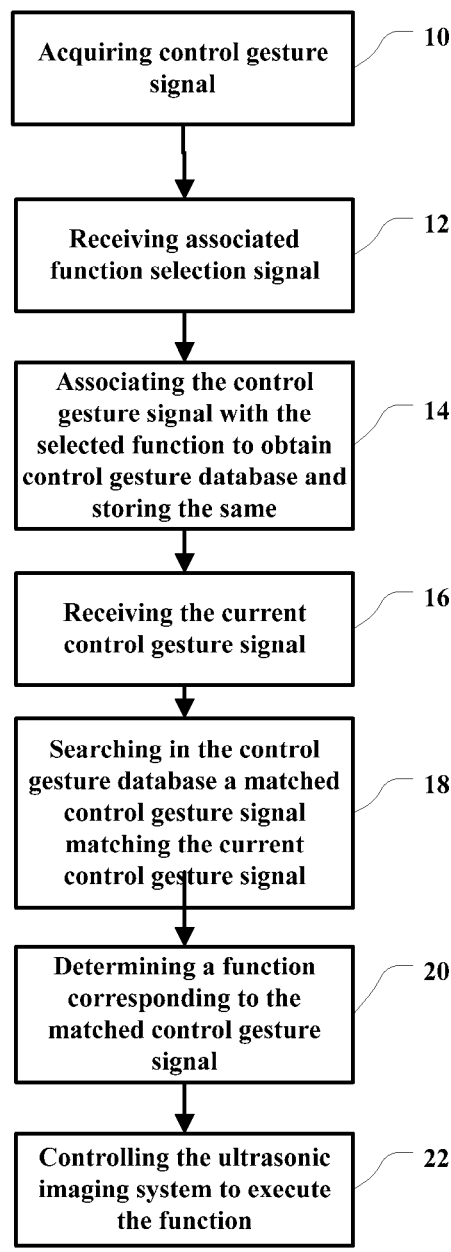
FIG. 2 is a flow chart of a method of controlling an ultrasonic imaging system according to one embodiment of the present disclosure.

FIG. 2 is a flow chart of a method of controlling an ultrasonic imaging system according to one embodiment of the present disclosure, the detailed steps of which will be described in detail hereinafter.

In one embodiment of the present disclosure, a control gesture signal and function association database may be established at first. That is, according to the user's operation habit or preference, the user can associate the functions of the ultrasonic system selected by the user with the control gesture signals selected or defined by the user to form a database, which can be used later to control the work of the ultrasonic imaging system when the ultrasonic imaging system is in operation.

For example, in Step 10, the control unit 8 may acquire control gesture signals. The control gesture signals herein represent control gestures performed by the user. The control gesture signals herein acquired by the control unit 8 may be the ones corresponding to the control gestures selected or defined by the user.

In one embodiment of the present disclosure, the control gesture signal acquired by the control unit 8 may be selected from a pre-stored control gesture signal database. In other words, a control gesture signal database is pre-stored in the ultrasonic imaging system or other apparatus. The control gesture signal database includes at least one predetermined control gesture signal, and each control gesture signal in the database represents at least one control gesture. The control unit 8 may select at least one control gesture signal from the control gesture signal database as the acquired control gesture signal by the control unit 8, and then associate the selected (acquired) control gesture signal with the function of the ultrasonic imaging system selected by the user. The detailed association process will be described below.

In one embodiment of the present disclosure, the selection of the control gesture signal from the control gesture signal database may be automatically performed by the control unit 8. Alternatively, a series of control gesture signals selected from the control gesture signal database by the control unit 8 can be displayed on the display unit 7 for the user to view and select; thus the selection of the control gesture signal may be manually completed by receiving a user input selection signal.

In embodiments of the present disclosure, the aforementioned control gesture signal database may be stored in a memory of the ultrasonic imaging system or in a portable storage device (for example, a portable storage device communicating with the control unit 8 and/or the ultrasonic imaging system via a communication interface such as a USB port), or stored in another remote medical apparatus or electronic apparatus (for example, a computer, a workstation, another ultrasonic imaging equipment or other type of medical apparatus, or a cloud storage system communicating with the control unit 8 and/or the ultrasonic imaging system via a wired network or wireless network).

In some other embodiments of the present disclosure, the control gesture signal acquired by the control unit 8 may be customized by the user. For example, the control unit 8 may receive from the first input unit 9 a control gesture signal input by the user. In other words, the user may input a user-defined control gesture through the first input unit 9, and then the first input unit 9 transforms the user-defined control gesture into a control gesture signal and outputs the control gesture signal. The control unit 8 may receive the control gesture signal corresponding to the user-defined control gesture from the first input unit 9. Then the control unit 8 may associate the control gesture signal, i.e., the user-defined control gesture signal, with the function of the ultrasonic imaging system selected by the user. The association process will be described below in detail.

In the embodiments of the present disclosure, the first input unit 9 may be any kind of appropriate input unit that is capable of transforming the control gesture into the control gesture signal which can be recognized by the ultrasonic imaging system or the control unit 8. Correspondingly, the control gesture signal output by the input unit 9 may be a signal in any appropriate form or format, which is not limited herein, as long as it can be recognized or identified by the ultrasonic imaging system or the control unit 8.

For example, in one exemplary embodiment of the present disclosure, the first input unit 9 may be a touch screen, and correspondingly, the control gesture signal herein may be a signal generated by the touch screen when receiving a slide operation by the user. The touch screen may detect various slide operations (i.e., the control gesture) on the touch screen to generate corresponding signals (i.e., the control gesture signals). Each kind of slide operation of the user (i.e., each kind of control gesture) may generate a corresponding control gesture signal. The detection of the user's operation by the touch screen and transformation of the operation to corresponding signals can be implemented by any suitable method.

Alternatively, in another exemplary embodiment of the present disclosure, the first input unit 9 may be a body motion controller, and correspondingly, the control gesture herein may be a signal generated by a body motion sensor through detecting a body motion (i.e., the control gesture) of the user. The body motion sensor may detect a particular body motion of the user (i.e., the control gesture) to generate corresponding signals (i.e., the control gesture signals). Each kind of body motion of the user (i.e., each kind of control gesture) may generate a corresponding control gesture signal. The detection of the user's body motion by the body motion controller and transformation of the body motion to corresponding signals may be implemented using any suitable method.

It should be understood that, in other embodiments of the present disclosure, the first input unit 9 may comprise other appropriate input devices that are capable of detecting and recognizing the control gesture input by a user.

The control operation and the corresponding signal thereof are described herein as a "control gesture" and "control gesture signal"; however, the control operation is not limited to those operations that are performed by hand. On the contrary, the control gesture herein may be any kind of control motion (for example, a control motion performed by hand, by other body limb, or by movement of appropriate assistant devices other than the body, etc.), as long as the control motion can control the working of the ultrasonic imaging system. Nevertheless, the control motions are still uniformly described herein as "control gestures."

In one exemplary embodiment of the present disclosure, the first input unit 9 may be a component integrated in the ultrasonic imaging system, or a separate component connected with the ultrasonic imaging system via a data transmission channel, e.g., a wired or wireless network.

In step 12, the control unit 8 may receive the associated function selection signal from the second input unit 10. The associated function selection signal may be used for the selection of at least one function of the ultrasonic imaging system, for example, one or a plurality of functions, or a series of functions, such as B-mode imaging, C-mode imaging, image freezing, image zooming, image rotation, parameter measurement, control panel raising, control panel descent, control panel rotation, display raising, display descent, display rotation and/or any other functions of the ultrasonic imaging system.

In one exemplary embodiment of the present disclosure, the aforementioned "function" of the ultrasonic imaging system can be any function and/or operation that can be executed by the ultrasonic imaging system, including all kinds of functions that are executed by internal hardware and/or software of the ultrasonic imaging system, such as various types of ultrasound scanning, signal processing, imaging processing, data communication with other remote systems or sub-systems, and physical operation executed by the ultrasonic imaging system itself, such as moving the ultrasonic imaging system forward or backward; raising, descent, rotation, or leaning of the display or the control panel; etc.

In the embodiments of the present disclosure, the associated function selection signal may be any one or more functions of all the functions of the ultrasonic imaging system.

In the embodiments of the present disclosure, the second input unit 10 receiving the associated function selection signal may be any appropriate input unit, e.g., a touch screen, button(s) or trackball on the control panel of the ultrasonic imaging system. For example, the user may input the associated function selection signal by touching the corresponding area of the touch screen, or pressing the button or trackball on the control panel.

In one exemplary embodiment of the present disclosure, the second input unit 10 may be a component integrated in the ultrasonic imaging system, or a separate component connected with the ultrasonic imaging system via a data transmission channel. For example, the second input unit 10 may be a remote input unit connected with the ultrasonic imaging system through a wired network or a wireless network.

In one exemplary embodiment of the present disclosure, the first input unit 9 and the second input unit 10 may be the same component/device or integrated in the same device, or they may be different components/devices separated from each other.

In one exemplary embodiment of the present disclosure, the sequence of Step 10 and Step 12 can be reversed. Step 10 may be carried out first and followed by Step 12, or Step 12 may be carried out first and followed by Step 10.

After receiving the associated function selection signal and the control gesture signal, in Step 14 the control unit 8 can associate the control gesture signal with the at least one function of the ultrasonic imaging system selected by the associated function selection signal, so as to obtain an association (e.g., from a database) between the control gesture signal and the at least one function of the ultrasonic imaging system. In other words, the control unit 8 can map the control gesture signal to the corresponding selected at least one function, so that the control gesture signal may be mapped to the selected at least one function. The association correlation between the control gesture signal and the at least one function may be presented in any appropriate form, for example, a lookup table.

Then, the control unit 8 may store the association correlation between the control gesture signal and the selected at least one function, such as the aforementioned lookup table, in control unit 8 or in memory in other parts of the ultrasonic imaging system, so as to form a control gesture signal and function association database.

In one exemplary embodiment of the present disclosure, the control gesture signal and function association database may include at least one control gesture signal and an association correlation between the control gesture signal and a function of the ultrasonic imaging system.

In the embodiments of the present disclosure, by adoption of the aforementioned steps, users can define by themselves any type of control gesture and select any function to be associated with the control gesture according to their own habits and preferences. The control gesture signal of the user-defined control gesture and the association correlation between the control gesture signal and the function of the ultrasonic imaging system may be stored in memory to form a control gesture signal and function association database. The control gesture signal and function association database may include any quantity of control gesture signals and association correlations between the control gesture signals and functions of the ultrasonic imaging system, which can be used in later controlling of the ultrasonic imaging system.

In the embodiments of the present disclosure, the control gesture may be any motion performed by the user or specific assistant facility, which may be decided entirely by the user and is not limited in the present disclosure.

When the ultrasonic imaging system is in normal operation, the user can control the ultrasonic imaging system by using the control gesture signal and function association database.

For example, when the ultrasonic imaging system is in normal operation, if the user expects to operate the ultrasonic imaging system in a certain manner to perform a certain function, the user can perform a certain control gesture. Then the first input unit 9 (e.g., a touch screen or a body motion controller) can detect or sense the current control gesture performed by the user, and generate a corresponding signal (i.e., the current control gesture signal).

Therefore, in Step 16, the control unit 8 may receive the current control gesture signal from the first input unit 9. The current control gesture signal represents the current control gesture performed by the user.

After receiving the current control gesture signal, in Step 18 the control unit 8 may search in the aforementioned control gesture signal and function association database for a control gesture signal matching the current control gesture signal. The control gesture signal in the control gesture signal and function association database that matches the current control gesture signal may be referred to as a "matched control gesture signal" herein. For example, the control unit 8 may compare the received current control gesture signal with the control gesture signal in the control gesture signal and function association database. When the current control gesture signal is identical or similar (e.g., similarity is greater than a predetermined threshold) to a certain control gesture signal, the certain control gesture signal may be determined to be the matched control gesture signal.

As previously described in the present disclosure, each of the control gesture signals in the control gesture signal and function association database is associated with at least one function of the ultrasonic imaging system, and the corresponding association correlations have already been stored in the control gesture signal and function association database. Thus, after the matched control gesture signal is found via searching in the control gesture signal and function association database, it is easy to obtain the function of the ultrasonic imaging system corresponding to or associated with the matched control gesture signal according to the control gesture signal and function association database, e.g., by searching in the aforementioned lookup table. Therefore, after obtaining the matched control gesture signal, in Step 20 the control unit 8 can easily determine at least one function of the ultrasonic imaging system associated with the matched control gesture signal, according to the association correlation between the matched control gesture signal and the at least one function of the ultrasonic imaging system stored in the control gesture signal and function association database; i.e., the control unit 8 can determine which function of the ultrasonic imaging system is associated with the matched control gesture signal.

Then, in Step 22, the control unit 8 may control the ultrasonic imaging system to perform the at least one function associated with the matched control gesture signal. For example, the control unit 8 may send to a corresponding component of the ultrasonic imaging system a control signal corresponding to the at least one function, so as to control the ultrasonic imaging system to initiate a corresponding function and/or perform a corresponding activity. For example, the control unit 8 may control the ultrasonic imaging system to power-on (in this case, although the ultrasonic imaging system may be turned off, the control unit 8 and the first input unit 9 may keep operating, so as to detect whether the user inputs a control gesture, and when detecting the control gesture input by the user associated with the power-on function, the control unit 8 can send a power-on signal to power-on the whole ultrasonic imaging system), start-up a certain mode of ultrasonic imaging, freeze an image, perform all kinds of image processing and measurements, perform various kinds of movement of the display and/or the control panel (e.g., lift up, lower, lean and/or rotate), or turn off the ultrasonic imaging system.

In some embodiments of the present disclosure, the control unit 8 may be either an individual discrete component, or integrated with other devices (e.g., the data processing unit 6, etc.) of the ultrasonic imaging system.

According to embodiments of the present disclosure, clinicians are enabled to define personalized control gestures according to their own operation routines and habits to form an association correlation database of control gesture signals and functions, such that when the ultrasonic imaging system is in operation, a clinician may control the ultrasonic imaging system by simply performing the corresponding control gesture to control the ultrasonic imaging system to execute the corresponding function. Therefore, it is unnecessary for clinicians to pay attention to the keyboard on the control panel; they can instead focus on the images on the monitor or the control of the probe. Therefore, the present disclosure may greatly facilitate user operation.

The foregoing embodiments with detailed descriptions represent several implementations of the present disclosure, but they should not be construed as limiting the scope of the present disclosure. It should be understood that, for those skilled in the art, a number of modifications and improvements can also be made without departing from the concepts of the present disclosure which are within the claimed scope of the present disclosure. In addition, the phrase "one embodiment" may represent different embodiments, and all embodiments or a part of them can be combined in one embodiment.

We claim:

1. A method for controlling an ultrasonic imaging system, comprising:
   when the ultrasonic imaging system is in a mode of associating gestures with functions of the ultrasonic imaging system:

acquiring a control gesture signal by at least one of:
  in response to a user performing a control gesture, automatically selecting a control gesture signal from a pre-stored control gesture signal database corresponding to the performed control gesture;
  receiving a user selection of a control gesture signal from a series of displayed control gestures from the pre-stored control gesture signal database; or
  receiving a custom control gesture signal in response to the user performing a custom gesture;
receiving a user selection of at least one function from a plurality of function options, said function options including one or more function keys on a control panel and/or a one or more functions from a menu on a user interface wherein the at least one selected function selected is a function of the ultrasonic imaging system;
associating the acquired control gesture signal with the at least one selected function to obtain an association correlation between the control gesture signal and the selected function;
repeating the steps of acquiring a control gesture signal, receiving a user selection of the at least one function, and associating the acquired control gesture signal with the at least one selected function to establish a control gesture signal and function association database, wherein the database stores multiple control gesture signals and association correlations; and
when the ultrasonic imaging system is in normal operation:
  receiving a current control gesture signal for a gesture performed by the user;
  searching in the control gesture signal and function association database for a control gesture signal matching the current control gesture signal to obtain a matched control gesture signal;
  determining at least one function associated with the matched control gesture signal according to the association correlation of the matched control gesture signal; and
  controlling the ultrasonic imaging system to execute the at least one function associated with the matched control gesture signal.

2. The method of claim 1, wherein the control gesture signal is a signal generated by a slide operation of the user on a touch screen.

3. The method of claim 1, wherein the control gesture signal is a signal generated by a body motion sensor which detects body movement of the user.

4. The method of claim 1, wherein the control gesture signal and function association database comprises at least one control gesture signal and an association correlation between the control gesture signal and a function of the ultrasonic imaging system.

5. An ultrasonic imaging system comprising:
a data processing unit;
at least one input unit connected to the data processing unit,
wherein, when the ultrasonic imaging system is in a mode of associating gestures with functions of the ultrasonic imaging system, the data processing unit is configured to:
  acquire a control gesture signal using the at least one input unit by at least one of:
    in response to a user performing a control gesture, automatically selecting a control gesture signal from a pre-stored control gesture signal database corresponding to the performed control gesture;
    receiving a user selection of a control gesture signal from a series of displayed control gestures from the pre-stored control gesture signal database; or
    receiving a custom control gesture signal in response to the user performing a custom gesture;
  receive a user selection of at least one function from a plurality of function options using the at least one input unit, said function options including one or more function keys on a control panel and/or a one or more functions from a menu on a user interface, wherein the at least one selected function selected is a function of the ultrasonic imaging system;
  associate the acquired control gesture signal with the at least one selected function to obtain an association correlation between the control gesture signal and the selected function;
  repeating the acquiring of a control gesture signal, the receiving of a user selection of the at least one function, and the associating of the acquired control gesture signal with the at least one selected function to establish a control gesture signal and function association database, wherein the database stores multiple control gesture signals and association correlations;
wherein, in normal operation, the data processing unit is further configured to:
  receive a current control gesture signal from the at least one input unit;
  search for a control gesture signal matching the current control gesture signal in the control gesture signal and function association database to obtain a matched control gesture signal;
  determine at least one function associated with the matched control gesture signal according to the association correlation of the matched control gesture signal; and
  controls the ultrasonic imaging system to perform the at least one function associated with the matched control gesture signal.

6. The system of claim 5, wherein the at least one input unit is a touch screen.

7. The system of claim 5, wherein the at least one input unit is a body motion controller.

8. The system of claim 5, wherein the control gesture signal and function association database comprises at least one control gesture signal and an association correlation between the control gesture signal and a function of the ultrasonic imaging system.

9. The method of claim 1, wherein the at least one selected function comprises a plurality of selected functions, and wherein acquired control gesture signal is associated with the plurality of selected functions.

10. The method of claim 1, wherein the control gesture signal and function association database is stored in a remote apparatus accessible to the ultrasonic imaging system via a network.

11. The system of claim 5, wherein the at least one selected function comprises a plurality of selected functions, and wherein acquired control gesture signal is associated with the plurality of selected functions.

12. The method of claim 5, wherein the control gesture signal and function association database is stored in a remote apparatus accessible to the ultrasonic imaging system via a network.

* * * * *